(12) United States Patent
Wruck et al.

(10) Patent No.: US 11,623,064 B2
(45) Date of Patent: Apr. 11, 2023

(54) DISPENSING DEVICE FOR INTRODUCING AN ANESTHETIC INTO A BREATHING GAS STREAM

(71) Applicant: Drägerwerk AG & Co. KGaA, Lübeck (DE)

(72) Inventors: Norbert Wruck, Lübeck (DE); Michael Riecke, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 906 days.

(21) Appl. No.: 16/316,865

(22) PCT Filed: Jul. 13, 2017

(86) PCT No.: PCT/EP2017/000834
§ 371 (c)(1),
(2) Date: Jan. 10, 2019

(87) PCT Pub. No.: WO2018/010845
PCT Pub. Date: Jan. 18, 2018

(65) Prior Publication Data
US 2019/0298965 A1    Oct. 3, 2019

(30) Foreign Application Priority Data

Jul. 14, 2016  (DE) .................... 10 2016 008 493.6

(51) Int. Cl.
*A61M 16/18* (2006.01)
*A61M 16/10* (2006.01)
(Continued)

(52) U.S. Cl.
CPC ........ *A61M 16/18* (2013.01); *A61M 16/0051* (2013.01); *A61M 16/109* (2014.02);
(Continued)

(58) Field of Classification Search
CPC .. A61M 16/18; A61M 16/109; A61M 16/145; A61M 16/203; A61M 16/0051;
(Continued)

(56) References Cited

U.S. PATENT DOCUMENTS

| 3,446,243 A | * | 5/1969 | Haupt | A61M 16/18 138/37 |
| 4,059,657 A | * | 11/1977 | Hay | A61M 16/18 261/104 |

(Continued)

FOREIGN PATENT DOCUMENTS

| CN | 101780302 A | 7/2010 |
| CN | 103357099 A | 10/2013 |

(Continued)

*Primary Examiner* — Kathryn E Ditmer
(74) *Attorney, Agent, or Firm* — McGlew and Tuttle, P.C.

(57) ABSTRACT

A dispensing device for dispensing anesthetic in a breathing gas stream includes a flow duct (42) for an anesthetic-containing breathing gas stream, a control unit (5) and a first temperature sensor (54). An anesthetic feed device (45) has an evaporation surface (46) arranged in the flow duct (42). The first temperature sensor (54) detects the temperature of the evaporation surface (46) and sends a first temperature signal (T1) to the control unit (5). A second temperature sensor (53) detects the temperature of the breathing gas stream in the flow duct (42) and sends a second temperature signal (T2) to the control unit (5). The control unit (5) is configured to determine an anesthetic concentration based on the first and second temperature signals (T1, T2).

19 Claims, 4 Drawing Sheets

(51) Int. Cl.
*A61M 16/14* (2006.01)
*A61M 16/20* (2006.01)
*A61M 16/00* (2006.01)

(52) U.S. Cl.
CPC ........ *A61M 16/145* (2014.02); *A61M 16/203* (2014.02); *A61M 16/108* (2014.02); *A61M 2016/1035* (2013.01); *A61M 2205/3313* (2013.01); *A61M 2205/3334* (2013.01); *A61M 2205/3368* (2013.01); *A61M 2205/3386* (2013.01); *A61M 2205/50* (2013.01)

(58) Field of Classification Search
CPC ........ A61M 16/108; A61M 2016/1035; A61M 2205/3313; A61M 2205/3334; A61M 2205/3368; A61M 2205/3386; A61M 2205/50; A61M 16/1075; A61M 16/14; A61M 16/16; A61M 16/161; F24F 6/02; F24F 6/025; F24F 6/08; F24F 6/10
See application file for complete search history.

(56) References Cited

U.S. PATENT DOCUMENTS

| | | | | |
|---|---|---|---|---|
| 4,477,395 | A * | 10/1984 | Albarda | A61M 16/147 261/131 |
| 4,587,966 | A | 5/1986 | Albarda | |
| 4,770,168 | A * | 9/1988 | Rusz | A61M 16/18 128/203.12 |
| 6,038,922 | A * | 3/2000 | Mauze | G01N 25/64 73/335.08 |
| 6,095,505 | A * | 8/2000 | Miller | A61M 16/164 261/130 |
| 6,202,480 | B1 * | 3/2001 | Mauze | G01N 25/64 374/109 |
| 6,464,941 | B1 * | 10/2002 | Diekmann | A61B 5/02154 422/82.05 |
| 2002/0113328 | A1 * | 8/2002 | Mulvaney | F24F 6/043 261/107 |
| 2006/0144395 | A1 * | 7/2006 | Koch | A61M 16/16 128/203.17 |
| 2006/0225735 | A1 * | 10/2006 | Bottom | A61M 16/18 128/203.12 |
| 2008/0190426 | A1 * | 8/2008 | Koch | A61M 16/1095 261/130 |
| 2009/0038614 | A1 * | 2/2009 | Kuo | A61M 16/1075 128/203.26 |
| 2009/0171514 | A1 | 7/2009 | Yyang et al. | |
| 2012/0248636 | A1 * | 10/2012 | Fridberg | A61M 16/109 261/128 |
| 2012/0318264 | A1 | 12/2012 | Jones et al. | |
| 2013/0072862 | A1 * | 3/2013 | Blackhurst | A61M 16/1095 604/24 |
| 2017/0319811 | A1 * | 11/2017 | Foote | A61M 16/142 |
| 2018/0250490 | A1 * | 9/2018 | Burgess | A61M 16/147 |

FOREIGN PATENT DOCUMENTS

| | | | |
|---|---|---|---|
| CN | 104144723 A | 11/2014 | |
| DE | 31 16 951 A1 | 12/1982 | |
| DE | 32 34 474 A1 | 3/1984 | |
| DE | 41 05 163 A1 | 8/1992 | |
| DE | 41 16 512 A1 | 11/1992 | |
| DE | 19646263 A1 * | 5/1998 | ............... F24F 6/10 |
| DE | 198 23 959 A1 | 1/1999 | |
| DE | 199 14 977 A1 | 10/1999 | |
| DE | 10105434 C1 * | 4/2002 | ........... A61M 16/18 |
| DE | 10 2007 037 955 A1 | 2/2009 | |
| DE | 10 2014 018 602 A1 | 6/2016 | |
| DE | 10 2015 000 175 B3 | 7/2016 | |
| EP | 88864 A * | 9/1983 | ........... A61M 16/00 |
| EP | 3 034 123 A1 | 6/2016 | |
| GB | 2255912 * | 11/1992 | |
| GB | 2255912 A | 11/1992 | |
| GB | 2 425 728 A | 11/2006 | |
| JP | 2012088018 A * | 5/2012 | |

* cited by examiner

DISPENSING DEVICE FOR INTRODUCING AN ANESTHETIC INTO A BREATHING GAS STREAM

CROSS REFERENCE TO RELATED APPLICATIONS

This application is a United States National Phase Application of International Application PCT/EP2017/000834, filed Jul. 13, 2017, and claims the benefit of priority under 35 U.S.C. § 119 of German Application 10 2016 008 493.6, filed Jul. 14, 2016, the entire contents of which are incorporated herein by reference.

TECHNICAL FIELD

The present invention pertains to a dispensing device for introducing an anesthetic into a breathing gas stream, which has a flow duct for the anesthetic-containing breathing gas stream, a control unit and a first temperature sensor.

BACKGROUND

Patients in operating rooms are anesthetized by means of anesthetics. In this case, the patients are supplied with breathing air by machines. These machines generate a so-called breathing gas, with which the anesthetic is mixed. The concentration of the anesthetic must be selected here such that the patient is anesthetized, without permanent injury or even death occurring.

There are carrier gas-dependent and carrier gas-independent systems. In carrier gas-independent systems, the anesthetic is measured out in the liquid or vapor state and then fed to the breathing gas stream.

In carrier gas-dependent systems, the anesthetic is introduced into the breathing gas system, e.g., by evaporation. The dose of the anesthetic mixed into the carrier gas is influenced here by the carrier gas stream and the temperature or the vapor pressure of the anesthetic in an evaporator chamber.

Anesthetic dispensers, which are pneumatically-mechanically connected to an anesthesia machine, are known. In this connection, only mechanical functioning parts are used for dispensing, wherein fine mechanical laminar flow elements (e.g., bypass and dispensing gaps) are used, the setting of which is carried out by means of mechanical temperature compensation elements, which are based on thermal linear expansion.

A complicated manual calibration of the bypass and dispensing gaps is necessary in these devices for a precise compliance with the required dispensing concentration. Further, high thermal storage masses are needed to keep temperature fluctuations as low as possible and to reach or obtain the saturation state for the breathing gas. In this connection, the breathing gas stream is selected such that it is fully saturated with anesthetic when it flows through the device.

The mechanical elements and fine mechanical elements cannot be electrically actuated, so that it is not possible to automatically regulate the dispensing concentration of the anesthetic at the breathing gas stream at different temperatures. Furthermore, the gas flows and the operating durations of the mechanical elements cannot be measured.

Detecting the anesthetic concentration in the breathing gas with optical media is also known. This optical measurement of the anesthetic concentration is, however, very expensive, prone to error and high-maintenance.

Monitoring the temperature of the anesthetic with a measuring element arranged on the outside at an anesthetic tank is known from GB 2 425 728. The temperature measured by the measuring element represents an approximate indication of the mean value of the vapor pressure of the anesthetic in the tank. Assumptions from tank-specific measurements, which must be included in the result of the concentration determination, must be made for the calculation of the concentration of the anesthetic. This method is inaccurate since it is supported on inaccurate assumptions.

SUMMARY OF THE INVENTION

Therefore, an object of the present invention is to create a device, which provides an accurate, cost-effective, electronic actuation for an anesthetic dispenser.

In the case of a dispensing device for anesthetic in a breathing gas stream cited in the introduction, provisions are made here according to the present invention for the dispensing device to have a feed device with an evaporation surface for anesthetic, which evaporation surface is arranged in the flow duct, wherein the first temperature sensor detects the temperature of the evaporation surface and sends a first temperature signal to the control unit, and the dispensing device has a second temperature sensor, which detects the temperature of the breathing gas stream in the flow duct and sends as second temperature signal to the control unit, wherein the control unit is configured to control an anesthetic concentration by means of the first and second temperature signals.

Thus, a "wet" temperature which is measured on the evaporation surface for anesthetic of the feed device and a "dry" temperature which is measured in the breathing gas stream of the flow duct are determined by means of the present invention. Since the evaporation surface of the feed device is arranged in the breathing gas stream, breathing gas constantly flows around it. As long as the breathing gas is 100% saturated with anesthetic, no additional anesthetic evaporates from the evaporation surface. Hence, a temperature, which corresponds to the temperature of the breathing gas stream, which is 100% saturated with anesthetic, is set at the evaporation surface.

As soon as the breathing gas stream is no longer 100% saturated with anesthetic because of a state change, the breathing gas stream, which is in contact with the evaporation surface, absorbs more anesthetic via evaporation. In this case, the breathing gas stream cools off the evaporation surface to a temperature, which is called the adiabatic temperature. This temperature requires a 100% saturation of the breathing gas stream with anesthetic. The temperature of the wet evaporation surface therefore corresponds to the temperature of the breathing gas with full anesthetic saturation before a mist state is reached.

Thus, the concentration of the anesthetic in the breathing gas stream can be determined by means of the first and second temperature signals, for example, analogously to the measurement principle of a psychrometer or, for example, by means of a Mollier h+,x diagram as described in more detail in regard to FIG. 3. An accurate determination of the concentration may also be carried out without a calibration in case of fluctuating temperatures, since the fluctuations of the temperature are taken into consideration in the determination of the anesthetic concentration. The determination of the anesthetic concentration in the breathing gas stream by means of the measurement of the first and second temperature signals can therefore be used universally and without calibration.

Further, thermal storage masses and expensive mechanical temperature compensation elements are as a result no longer needed. Anesthetic dispensers are consequently more lightweight and more cost-effective. Further, an electronic regulation of the anesthetic dispenser can be carried out with the present invention, so that an automatic control of the anesthetic concentration in the breathing gas stream to the patient can be carried out with the known anesthetic concentration at the outlet of the anesthetic dispenser. In this case, the control of the concentration can be brought about at any desired point after the measurement, e.g., by dilution with fresh breathing gas. As an alternative, the control unit may influence, e.g., the temperature of the breathing gas stream or of the anesthetic or the velocity of the breathing gas stream, to control the anesthetic concentration in the breathing gas stream. The first and second temperature sensors may be arranged in a flow duct downstream of an evaporator chamber. In this case, the evaporation surface is arranged downstream of a first evaporation surface of the evaporator chamber in a flow duct arranged downstream and is primarily used for determination of the wet temperature by the first temperature sensor, and it is wetted with anesthetic by the feed device. The first and second temperature sensors may, for example, also be arranged within the evaporator chamber, preferably downstream of the first half of the path of the flow duct through the evaporator chamber, for example, in an outlet area of the evaporator chamber. In these cases, the evaporation surface of the feed device is arranged in the evaporator chamber and may be identical to an evaporation surface of the evaporator chamber.

A definition of a term follows before going into more detail on advantageous variants.

A flow duct may be defined, on the one hand, as a common flow duct and, on the other hand, also as a split flow duct, wherein the two parts of the split flow duct are connected to one another in a fluid-communicating manner. The first and second temperature sensors may therefore also carry out the detection of the temperatures in different partial areas of a flow duct system.

The control unit advantageously has a determination module, which determines a state point of the anesthetic from the detected first and second temperature signals, the state point being associated with an anesthetic concentration in the breathing gas stream. The determination may be carried out by means of a state diagram, which is in this case stored in the determination module. In this way, the control unit can determine the concentration of the anesthetic in the breathing gas stream in a simple and rapid manner by means of the measurement of the two temperatures.

Provisions may advantageously be made for the control unit to have a calculation module, which is configured to determine a difference between the first and second temperature signals, wherein the control unit is configured to control the anesthetic concentration by means of the first and second temperature signals.

In this case, a difference in temperature may be determined between the first temperature and the second temperature. If a difference in temperature is determined, this indicates that the breathing gas stream is not 100% saturated with anesthetic. The control unit may take actions which return the breathing gas stream with anesthetic to 100% saturation, among other things, for example, on the basis of this difference in temperature and, for example, at the same time regulate and/or keep the second temperature at a desired value in order to set an anesthetic concentration. As an alternative or in addition, the control unit may be configured such that it allows the difference to be included in a psychrometric formula for the determination of the anesthetic concentration.

The anesthetic concentration can be determined with a high accuracy due to the detection of the "dry" and "wet" temperatures of the anesthetic in the flow duct.

The control unit advantageously has a calculation module, which is configured to determine a difference between the temperature signals, wherein the control unit has a regulating unit, which is configured to regulate the difference amount to a minimum.

The control unit advantageously has a desired value input for a desired value signal for the anesthetic concentration in the breathing gas stream and a regulating unit, which is configured to regulate the anesthetic concentration in a patient feed line to the desired value signal.

A user of the dispensing device may send a desired value for the anesthetic concentration to the control unit via the desired value input.

The dispensing device advantageously has an outflow valve, which is connected to the flow duct in a fluid-communicating manner and is controlled by the control unit.

In this case, the control unit may send a control signal to the outflow valve. Further, the outflow valve may open and close the flow duct. The size of the valve opening can be adjusted by the control unit as a function of the determined anesthetic concentration in the breathing gas stream.

The outflow valve may advantageously be a proportional valve which may preferably be configured as a cone valve.

A gradual change in the breathing gas flow in the flow duct is thus made possible. The breathing gas stream may be set with higher accuracy with the proportional valve.

It is further advantageous if the temperature sensors are configured as electric sensors, encapsulated or unencapsulated thermocouples, resistor elements or as NTC (Negative Temperature Coefficient) resistors.

Further, the temperature sensors may advantageously be configured as infrared detectors measuring in a contactless manner. As an alternative, they may have a one-piece configuration, in which case they are configured as a spatially resolving infrared sensor measuring in a contactless manner.

It is further advantageous that the dispensing device has an evaporator chamber, in which an anesthetic reservoir is arranged upstream of the evaporation surface, and the feed device is connected to the anesthetic reservoir in a fluid-communicating manner.

In this case, the breathing gas stream is guided through the evaporator chamber before it reaches the flow duct. The anesthetic reservoir may be configured as a tank open on one side. An anesthetic is stored in the anesthetic reservoir. The anesthetic is, as a rule, a volatile substance and is present in the liquid form. The breathing gas stream sweeps over the surface of the anesthetic on the open side of the tank, the surface of the anesthetic functioning as a main evaporation surface that is primarily used to introduce the anesthetic into the breathing gas stream. In this case, the anesthetic evaporates into the breathing gas stream and is built up in the breathing gas stream. The anesthetic reservoir further forms an anesthetic source for the feed device. The feed device guides the anesthetic from the anesthetic reservoir to the evaporation surface of the feed device, which is used for the measurement of the wet temperature by the first temperature sensor. In this way, a constant inflow of anesthetic through the feed device to the evaporation surface of the feed device is guaranteed.

The feed device is advantageously configured at least partially as a porous solid, sintered body, nonwoven fabric or fiber stocking.

A small quantity of anesthetic may in this way be stored in the feed device and evaporate from the evaporation surface. Further, the feed device may transport the anesthetic from the anesthetic source to the evaporation surface on the basis of capillary action. As an alternative, the feed device may also spray anesthetic onto the evaporation surface.

A fill level monitor for the evaporator chamber, which sends a fill level signal to the control unit, is further advantageously provided. With a fill level monitor, the control unit can automatically recognize when the anesthetic reservoir is depleted. The anesthetic reservoir must be filled up in this case.

It is further advantageous if the evaporator chamber has an inlet opening for the breathing gas, through which the breathing gas can flow into the evaporator chamber as breathing gas stream.

It is further advantageous if a heater, which heats the breathing gas stream before it enters into the evaporator chamber, is arranged upstream of the inlet opening. With the change in the temperature of the entering breathing gas stream, the dose of the anesthetic that is introduced into the breathing gas may be varied. The heater can be controlled by the control unit on the basis of the anesthetic concentration.

Further, an anesthetic heater, which is configured to heat the anesthetic in the anesthetic reservoir, may be comprised by the evaporator chamber, wherein the anesthetic heater is preferably controlled by the control unit and is preferably configured as a gas stream heater or radiant heater.

The dose of the anesthetic which is introduced into the breathing gas stream may likewise be varied with the change in the temperature of the anesthetic in the anesthetic reservoir.

The present invention further pertains to a process for controlling and/or regulating an anesthetic concentration in a breathing gas stream by means of the dispensing device for anesthetic according to the invention, with the steps: Detection of a temperature of the evaporation surface by means of a first temperature sensor; and detection of a temperature of the breathing gas stream in the flow duct by means of a second temperature sensor, and for controlling and/or regulating an anesthetic concentration in the breathing gas stream by means of the temperature of the breathing gas stream in the flow duct and the temperature of the evaporation surface by means of a control unit of the dispensing device.

The process advantageously has the following additional steps: Determination of the anesthetic concentration by means of the temperature of the evaporation surface and the temperature of the breathing gas stream in the flow duct by means of a determination module of the control unit; and regulation of the breathing gas stream on the basis of the anesthetic concentration by means of a regulating unit of the control unit.

The process advantageously comprises the determination of the temperature difference between the temperature of the evaporation surface and the temperature of the breathing gas stream in the flow duct by means of a calculation module of the control unit; and the regulation of the anesthetic concentration by means of the dispensing device on the basis of the temperature difference by means of a regulating unit.

It may also be considered to be advantageous that the anesthetic concentration is determined by means of the temperatures of the breathing gas stream and of the evaporation surface and by means of a state diagram for the anesthetic.

A corresponding value for the concentration is determined by means of the state diagram for the first and second temperature signals. See, for this, analogously the remarks made concerning the dispensing device and, for example, the remarks made concerning FIG. 3. The concentration may thus be determined rapidly and accurately without great effort.

Furthermore, reference is analogously made to the description about the dispensing device cited above with regard to the variants of the process.

An exemplary embodiment of the present invention is explained in more detail below on the basis of the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
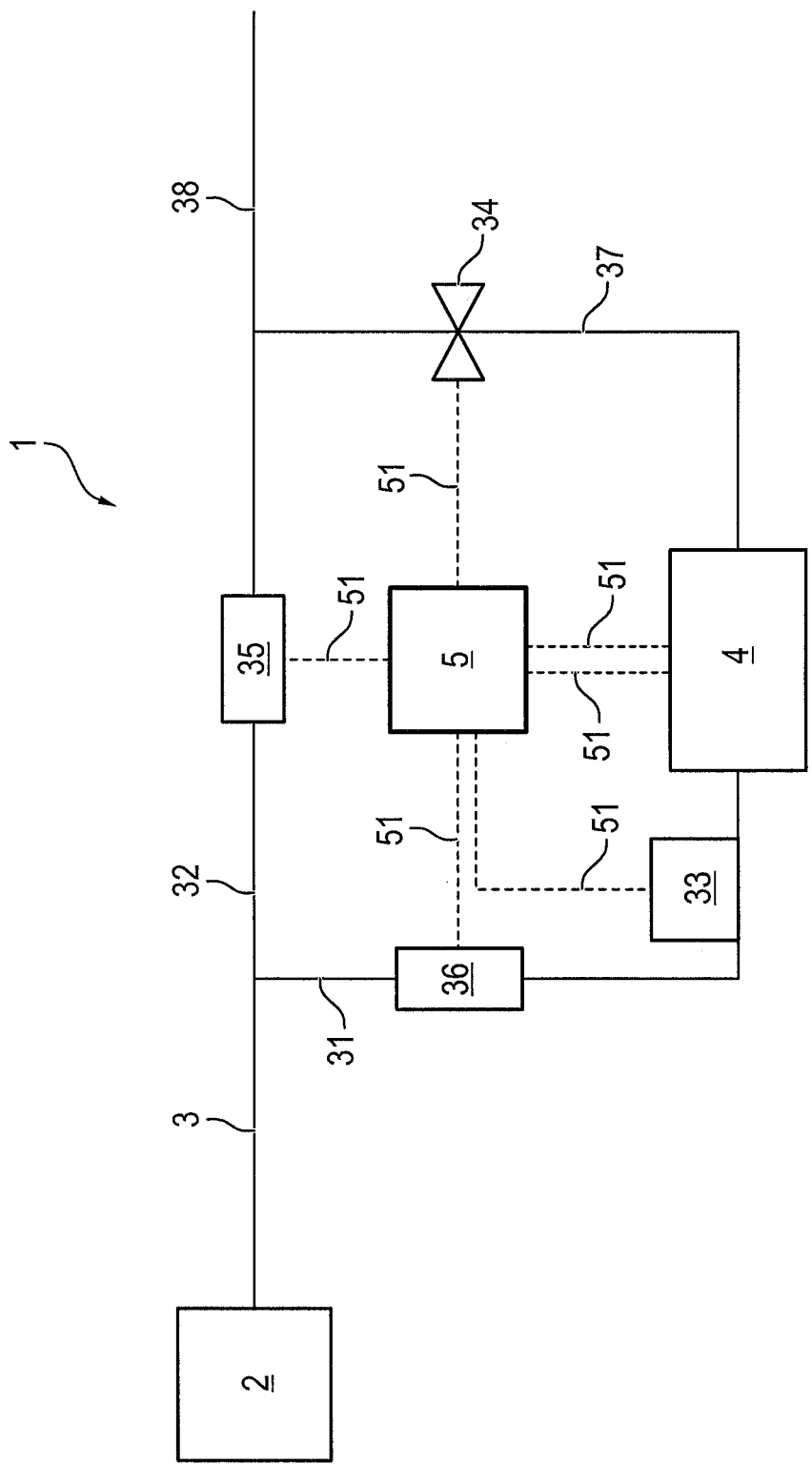
FIG. 1 is a schematic view showing a dispensing device for anesthetic.

Referring to the drawings, a dispensing device is designated below in its entirety by the reference number 1. FIG. 1 shows a schematic overview diagram of the dispensing device 1. The dispensing device 1 provides a breathing gas stream, which contains an anesthetic, to a patient.

The dispensing device 1 has a gas mixer 2 for providing a breathing gas stream, which still does not contain anesthetic. The breathing gas stream is mixed in the gas mixer 2 as needed and introduced into a gas line system 3.

The breathing gas stream is guided into an evaporator chamber 4 for an anesthetic via a feed line 31 through an inflow opening 41. Anesthetic evaporates in the evaporator chamber 4 and is absorbed by the breathing gas stream.

A connecting line 37 guides the breathing gas stream mixed with anesthetic from the evaporator chamber 4 into a patient feed line 38, which guides it further to the patient. Further, a bypass line 32 is provided, which guides the anesthetic-free breathing gas stream from the gas mixer 2 past the feed line 31, the evaporator chamber 4 and the connecting line 37 to the patient feed line 38. In the patient feed line 38, the breathing gas stream from the bypass line 32, which contains no anesthetic, is mixed with the breathing gas stream from the connecting line 37, which contains anesthetic. The concentration of the anesthetic in the breathing gas stream of the connecting line 37 as well as the relationship between the breathing gas streams from the bypass line 32 and from the connecting line 37 determine the concentration of the anesthetic in the patient line 38.

Figure 2A:
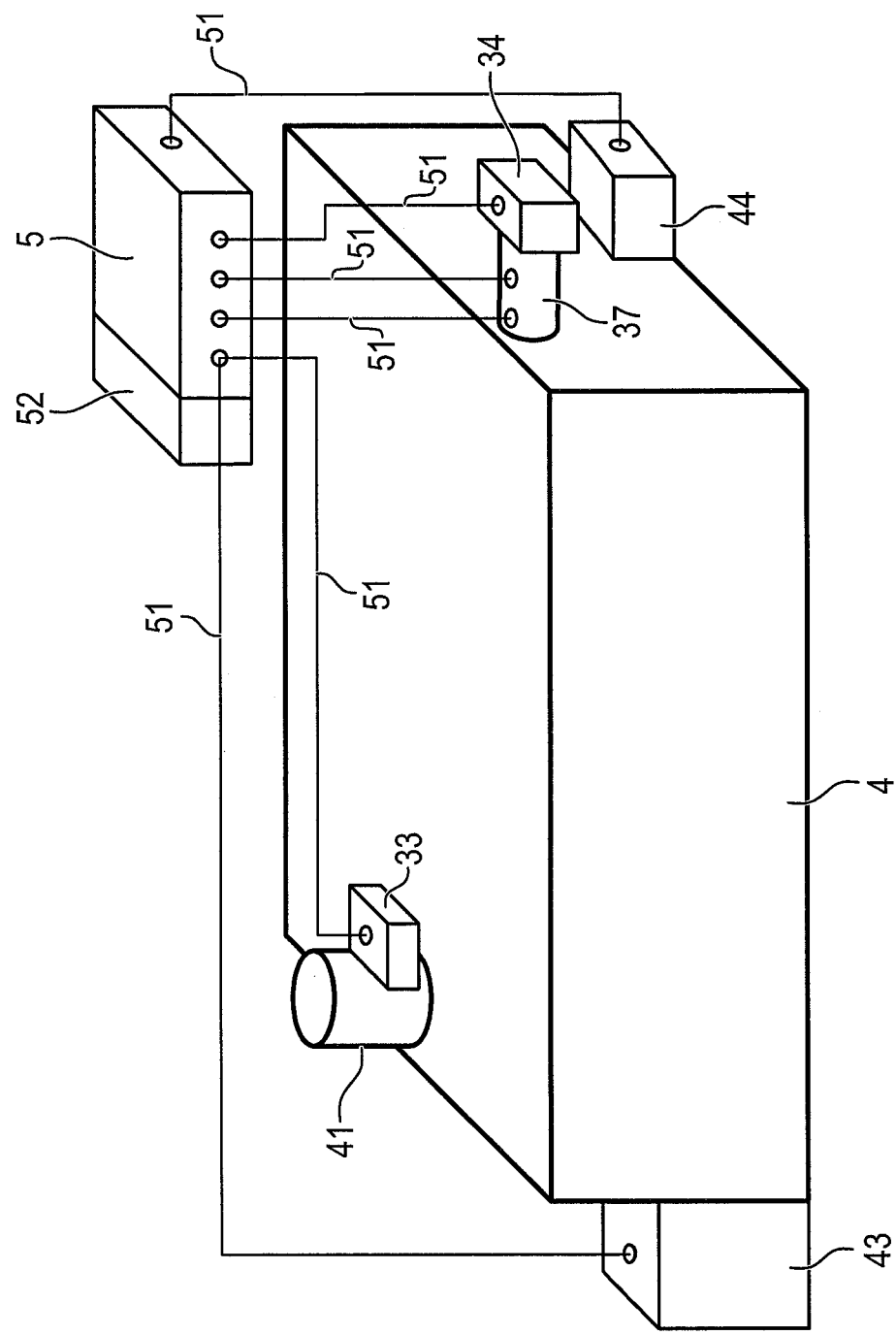
FIG. 2a is an external perspective schematic view showing an evaporation chamber with control unit.
Figure 2B:
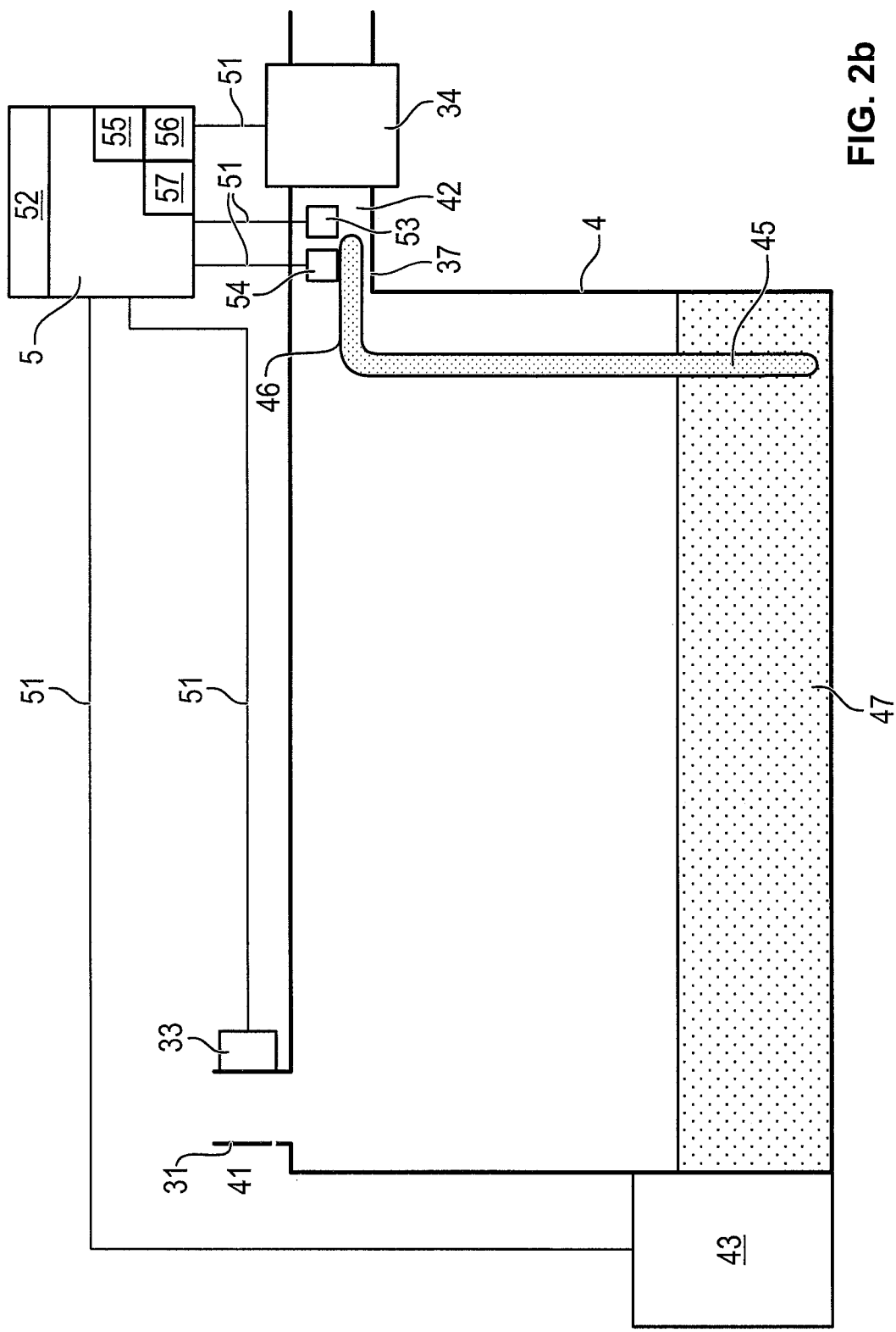
FIG. 2b is a schematic sectional view showing the evaporation chamber with control unit.

According to FIG. 2b, the evaporator chamber 4 has an anesthetic reservoir 47. An anesthetic is arranged in the anesthetic reservoir 47. The breathing gas from the feed line 31 is introduced into the evaporator chamber 4 via an inflow opening 41 and flows over the open anesthetic reservoir 47, i.e., the surface of the anesthetic stored in it. In this case, the breathing gas stream which flows over the anesthetic reservoir 47 absorbs the evaporating anesthetic. The breathing gas stream mixed with anesthetic flows further through a flow duct 42 into the connecting line 37. Accordingly, the flow duct 42 is arranged downstream of the anesthetic reservoir 47.

Further, a feed device 45, which has an evaporation surface 46, is provided. The feed device 45 is connected to the anesthetic reservoir 47 and delivers anesthetic from the anesthetic reservoir 47 to the evaporation surface 46.

In this connection, the feed device 45 may be configured as a wick. The wicking material may be a nonwoven fabric or a fiber stocking. Other materials that have a capillary action may also be used. In order to limit the evaporation of the anesthetic from the wicking material onto the evaporation surface 46, the remaining surface of the feed device 45 may be provided with a protective jacket, which may be configured, e.g., as a metal pipe.

The evaporation surface 46 is arranged in the flow duct 42. The breathing gas stream, which is mixed with anesthetic, sweeps over the evaporation surface 46.

In a first alternative mode of operation the breathing gas stream is fully saturated with anesthetic when it flows through the evaporator chamber 4. Accordingly, the saturation of the breathing gas stream with anesthetic is 100%. The breathing gas stream saturated 100% with anesthetic does not absorb any more anesthetic from the evaporation surface 46. The temperature of the evaporation surface 46 and the temperature of the breathing gas stream are therefore equal, i.e., the difference in temperature between the evaporation surface 46 and the breathing gas stream is minimal.

In a second alternative mode of operation, the breathing gas stream is not fully saturated with anesthetic when it flows through the evaporator chamber 4. When it sweeps over the evaporation surface 46, the breathing gas stream not fully saturated with anesthetic cools off this evaporation surface 46. The cooling off takes place by evaporation of the anesthetic in the breathing gas stream. The breathing gas stream not fully saturated with anesthetic, which sweeps over the evaporation surface 46, thus consequently absorbs more anesthetic over the evaporation surface 46. The portion of the breathing gas stream, which sweeps over the evaporation surface 46, is very small. There is therefore no significant increase in the anesthetic concentration over the evaporation surface 46 in the entire breathing gas stream.

The cooling off of the evaporation surface 46 by the breathing gas stream not fully saturated with anesthetic may in this case only take place until the breathing gas stream, which sweeps over the evaporation surface 46, is fully saturated with anesthetic.

In both modes of operation, a first temperature sensor 54 and a second temperature sensor 53 are provided in the flow duct 42. The second temperature sensor 53 determines the temperature of the breathing gas stream flowing through the flow duct. The first temperature sensor 54 determines the temperature of the evaporation surface 46. Thermal fluctuations in the evaporator chamber 4 are automatically taken into account by the temperature measurements of the temperature sensors 53, 54.

The first and second temperature sensors 54, 53 may be arranged directly in the flow duct in a first alternative embodiment, wherein the first temperature sensor 54 may be in contact with the evaporation surface 46. In this case, the temperature sensors 53, 54 may be configured as electric sensors, encapsulated thermocouples, unencapsulated thermocouples, resistor elements or NTC resistors.

In a second alternative embodiment, the first and second temperature sensors 54, 53 may also determine the temperature in a contactless manner. At least one of the temperature sensors 53, 54 may be configured as an infrared detector in this embodiment.

In a third alternative embodiment, the first and second temperature sensors 54, 53 may be combined into a one-piece temperature sensor measuring in a contactless manner. In this case, the one-piece temperature sensor may be configured as a spatially resolving infrared sensor, which observes the evaporation surface 46 and the breathing gas stream at a distance from the evaporation surface 46. The part of the spatially resolving infrared sensor, which observes the evaporation surface, is defined here as the first temperature sensor 54, and the other part of the spatially resolving infrared sensor, which observes the dry breathing gas stream, is defined as the second temperature sensor 53.

The first and second temperature sensors 54, 53 generate temperature signals T1, T2, which are sent to a control unit 5 via signal lines 51.

For the first mode of operation, the control unit 5 has a calculation module 56, which determines the difference in temperature between the first and second temperature signals T1, T2. Further, the control unit 5 has a regulating unit 57, to which the calculation module 56 sends a temperature difference signal. In the first mode of operation, the regulating unit 57 is configured to minimize the difference in temperature, to regulate the difference in temperature to zero in the ideal case. In this case, the control unit 5 predefines a command variable for the regulating unit 57.

The control unit 5 further determines the concentration of the anesthetic in the breathing gas stream from the temperature signals of the temperature sensors 53, 54. For this purpose, the control unit 5 has access to a Mollier h+,x diagram of the anesthetic in question. The Mollier h+,x diagram may be stored in a determination module 52, which is connected to the control unit 5 such that the control unit 5 may read out the determination module 52. As an alternative, a Carrier diagram may also be used. Further, as an alternative, a formulaic connection or another suitable state diagram of the anesthetic used may also be used for the determination of the anesthetic concentration in the breathing gas.

In the second mode of operation, the regulating unit 57 is configured to regulate the concentration of the anesthetic in the breathing gas stream on the basis of the temperature data. The temperature data may in this case be determined from the temperature signal T1 of the first temperature sensor 54 or from the difference of the temperature signals T1, T2 of the first and second temperature sensors 54, 53.

The regulating unit 57 is connected via an additional signal line 51 to an outflow valve 34, which is arranged in the connecting line 37. The outflow valve 34 may close or open the connecting line 37. Further, the outflow valve 34 may bring about a partial opening of the connecting line 37.

The outflow valve 34 may be configured here as a proportional valve. In this connection, different subvariants of the proportional valve, for example, a cone valve, may also be used.

The outflow valve 34 sends its opening state via a signal line 51 to the control unit 5. The control unit 5 determines an opening desired value for the outflow valve 34 from the determined anesthetic concentration in the breathing gas stream. The opening desired value is sent to the outflow valve 34 when it deviates from the opening actual value of the outflow valve 34. The mixing ratio between the breathing gas streams from the bypass line 32 and the connecting line 37 may be controlled in this way. The anesthetic concentration in the breathing gas stream may thus be controlled in the patient feed line 38 in this way.

The control unit 5 receives from the operating personnel of the dispensing device 1 a desired value signal for the anesthetic concentration in the breathing gas via a desired value input 55. On the basis of the inputted desired value and of the anesthetic concentration determined in the breathing gas stream, the opening of the outflow vale 34 is controlled by the control unit 5.

The control unit 5 may further be connected via signal lines 51 to the flow resistors 35, 36 in the gas line system 3. Thus, a first flow resistor 35 may be provided in the bypass line 32, wherein the first flow resistor 35 may be controlled by the control unit 5. The breathing gas stream in the bypass line 32 may thus be controlled by the control unit 5 by means of the flow resistor 35 such that a desired anesthetic concentration is obtained from the evaporator chamber 4 after mixing with the breathing gas stream from the connecting line 37.

Further, a second controllable flow resistor 36 may be provided in the feed line 31 to the evaporator chamber 4. The second flow resistor 36 is likewise connected via a signal line 51 to the control unit 5. In this way, the control unit can influence the breathing gas stream in the entire gas line system 3.

Further, a line heater 33, which heats the breathing gas stream flowing through the feed line 31, may be provided at the feed line 31 to the evaporator chamber 4. The line heater 33 may be connected via a signal line 51 to the control unit 5, so that the regulating unit 57 can regulate the line heater 33. The control unit 5 can thus influence the temperature of the breathing gas stream flowing through the evaporator chamber 4 via the regulating unit 57 and thus also influence the dose of the anesthetic that is absorbed into the breathing gas stream.

Further, an anesthetic heater 43 may be provided, which is arranged at the anesthetic reservoir 47. The anesthetic heater 43 is configured to heat the anesthetic in the anesthetic reservoir 47. The anesthetic heater 43 may also be connected via a signal line 51 to the regulating unit 57, so that the control unit 5 can influence the temperature of the anesthetic in the anesthetic reservoir 47 via the regulating unit 57. The dose of the anesthetic, which evaporates in the breathing gas stream, may also be influenced by the control unit 5 with the anesthetic heater 43.

According to FIG. 2a, a fill level monitor 44, which monitors the fill level of the anesthetic in the anesthetic reservoir 47, is further provided. The fill level monitor 44 monitors the fill level of the anesthetic reservoir 47 automatically and sends a fill level signal to the control unit 5 via a signal line 51. The control unit 5 can in this way determine whether or not the anesthetic reservoir 47 is empty. If the anesthetic reservoir 47 is empty, the control unit 5 may be configured to send a signal to the user of the dispensing device 1, which signals a refill need of the anesthetic reservoir 47. Further, the control unit 5 may in this case also close the feed line 31 and the connecting line 37 of the gas line system 3 and thus prevent the stream of breathing gas through the evaporator chamber 4. Furthermore, the detection of the temperatures by means of the temperature sensors 53, 54 is then stopped, since an evaporation of anesthetic may no longer take place at the evaporation surface 46. Further, anesthetic is then also no longer present in the breathing gas stream, so that a determination of the concentration is unnecessary.

The determination of the concentration of the anesthetic in the breathing gas stream by means of a Mollier h+,x diagram is described below as an example.

Figure 3:
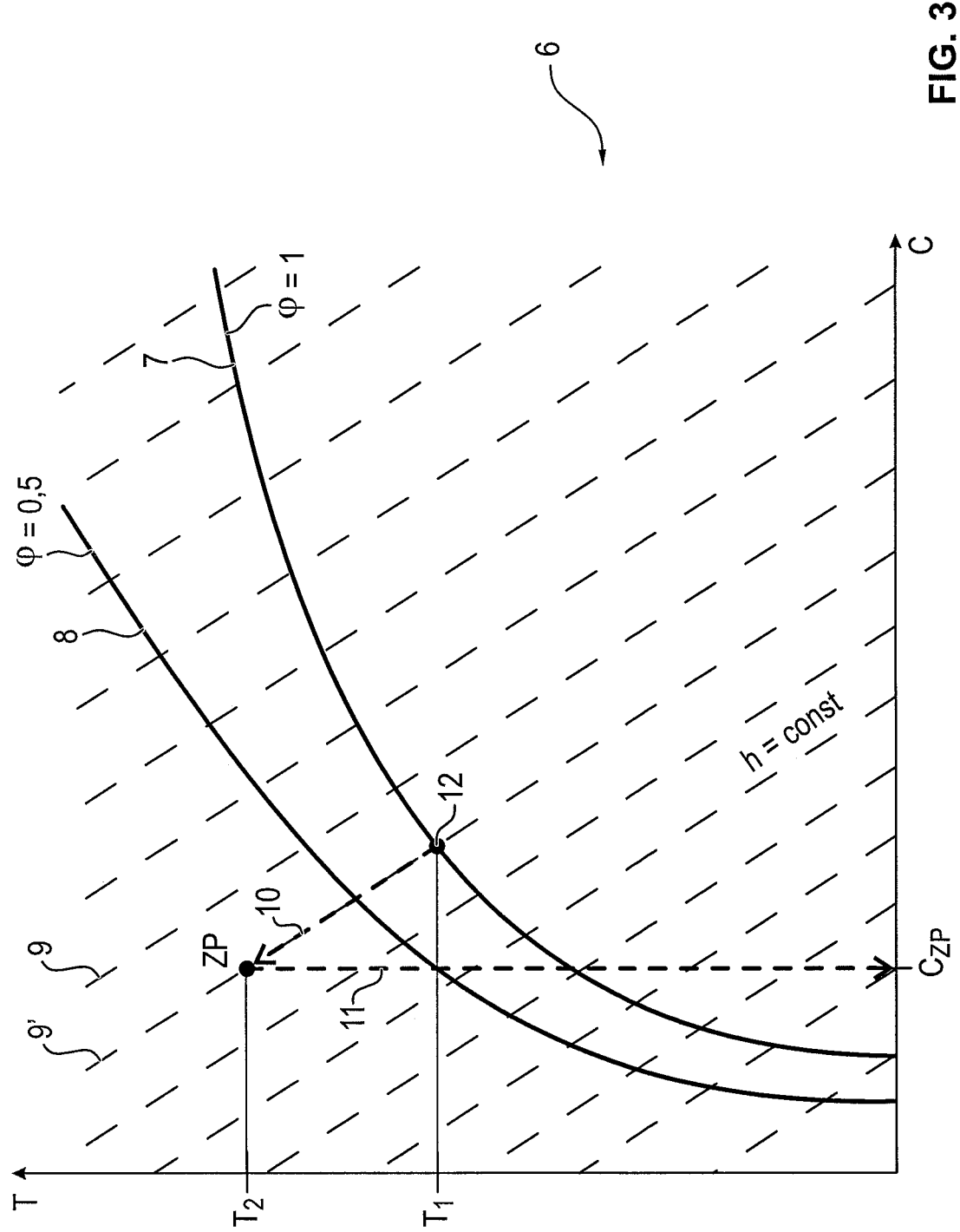
FIG. 3 is a state diagram of an anesthetic.

A Mollier h+,x diagram 6 is shown in FIG. 3. The temperature is plotted over the concentration. The 100% saturation curve 7, which indicates a 100% saturation of the breathing gas stream with anesthetic, is plotted. Below this curve is the mist area, in which the anesthetic would manifest as mist in the breathing gas stream. No mist forms above the 100% saturation curve 7. The further away a state point is located from the 100% saturation curve 7 in the upper area, the lower is the saturation of the breathing gas stream with anesthetic.

Furthermore, the 50% saturation curve 8, which shows a 50% saturation of the breathing gas stream with anesthetic, is plotted for illustration.

Furthermore, the so-called mist isotherms 9, which describe approximately adiabatic state changes in the diagram, are plotted. The enthalpy is approximately constant along a mist isotherm 9. The mist isotherms 9 are, as a rule, very steep, i.e., they run almost vertically. A change in the temperature therefore results in an almost equal concentration of the anesthetic in the breathing gas stream.

The temperature of the evaporation surface 46 in the flow duct 42, which is a "wet" temperature, is determined by means of the first temperature sensor 54. Therefore, the result is that the feed device 45 is wetted with the anesthetic, wherein the anesthetic evaporates from the evaporation surface 46 into the breathing gas stream. This first temperature is plotted as T1 in the diagram 6.

Because the first temperature T1 is measured on the evaporation surface 46 cooled by the breathing gas stream, the temperature of the evaporation surface 46 corresponds to the temperature of the breathing gas stream, which is in direct contact with the evaporation surface 46. The breathing gas stream which is in direct contact with the evaporation surface 46 is 100% saturated with anesthetic. Hence, the state point of the breathing gas saturated with anesthetic is known in the diagram 6. This state point is designated by the reference number 12 in the diagram 6 and lies on the curve 7.

The anesthetic and the breathing gas stream change their state adiabatically, if they move away from the evaporation surface 46, i.e., no heat exchange with the surrounding area takes place in case of the state change. The state change therefore takes place approximately along the mist isotherms 9'. This is identified by the arrow 10.

The control unit 5 determines with the second temperature sensor 53 a second temperature in the flow duct 42, which corresponds to the "dry" temperature of the breathing gas stream, wherein the breathing gas stream has a defined anesthetic concentration. This temperature is plotted as T2 in the diagram 6.

An adiabatic state change may be assumed between the breathing gas stream on the evaporation surface 46 and the dry breathing gas stream. Hence, both state points must lie on the same adiabats, which is approximated by the mist isotherm. The dry breathing gas stream therefore has a state that is located on these mist isotherms 9'. With the determined temperature T2 of the breathing gas stream and of the mist isotherms 9', the state point of the breathing gas stream mixed with anesthetic can be calculated in this way. The state change is highlighted by the arrow 10. Thus, knowing the temperature T2, the accurate concentration of the anesthetic in the breathing gas stream can be determined by means of the state point determined by the control unit 5 (see arrow 11).

Since the anesthetic concentration in the breathing gas stream is now known to the control unit 5, the control unit 5 can determine how the mixing ratio between the breathing gas stream in the bypass line 32 and the breathing gas stream with anesthetic in the connecting line 37 has to be provided by the evaporator chamber 4 in order to reach the desired value for the concentration of the anesthetic. Based on these values, the control unit 5 actuates the outflow valve 34. Further, the flow resistors 35, 36 as well as the heaters 33 and 43 may be actuated such that the corresponding anesthetic concentration in the breathing gas stream in the patient feed line 38 is set.

The calculation of the anesthetic concentration in the breathing gas stream of the patient feed line 38 may be carried out in real time by the control unit 5 by means of at most three material-specific calibration constants.

While specific embodiments of the invention have been shown and described in detail to illustrate the application of the principles of the invention, it will be understood that the invention may be embodied otherwise without departing from such principles.

The invention claimed is:

1. A dispensing device for anesthetic in a breathing gas stream, the dispensing device comprising:
   a flow duct for an anesthetic-containing breathing gas stream;
   a control unit;
   a first temperature sensor;
   an anesthetic feed device arranged in the flow duct, the anesthetic feed device comprising an anesthetic evaporation surface for evaporation of anesthetic in the flow duct, wherein the first temperature sensor is configured to detect the temperature of the anesthetic evaporation surface and is configured to send a first temperature signal to the control unit;
   a second temperature sensor for detecting a temperature of the breathing gas stream in the flow duct and configured to send a second temperature signal to the control unit, wherein the control unit is configured to control an anesthetic concentration in the breathing gas stream based on the first temperature signal and the second temperature signal;
   an evaporator chamber, in which an anesthetic reservoir is arranged upstream of the anesthetic evaporation surface, wherein the feed device is fluid-communicatingly connected to the anesthetic reservoir; and
   a connecting line connected to the evaporator chamber, the connecting line extending downstream of the evaporation chamber, the connecting line defining the flow duct, at least a portion of the anesthetic evaporation surface being located in the connecting line, wherein the first temperature sensor is configured to detect the temperature of the portion of the anesthetic evaporation surface, the second temperature sensor being configured to detect the temperature of the breathing gas stream in the connecting line.

2. The dispensing device in accordance with claim 1, wherein:
   the control unit comprises a determination module, which is configured to determine an anesthetic state point of anesthetic from the first temperature signal and the second temperature signal; and
   the state point is associated with a defined anesthetic concentration in the breathing gas stream.

3. The dispensing device in accordance with claim 1, wherein:
   the control unit comprises a calculation module, which is configured to determine a difference amount between the first temperature signal and the second temperature signal; and
   the control unit is configured to control the anesthetic concentration based on the difference amount between the first temperature signal and the second temperature signal.

4. The dispensing device in accordance with claim 3, wherein the control unit comprises a regulating unit, which is configured to regulate the difference amount to a minimum.

5. The dispensing device in accordance with claim 1, wherein the control unit comprises:
   a desired value input for input of a desired value signal for the anesthetic concentration in the breathing gas stream; and
   a regulating unit configured to regulate the anesthetic concentration in a patient feed line to the desired value signal.

6. The dispensing device in accordance with claim 5, further comprising an outflow valve, which is connected to the flow duct in a fluid-communicating manner and is configured to be regulated by the regulating unit.

7. The dispensing device in accordance with claim 6, wherein the outflow valve is configured as a proportional cone valve.

8. The dispensing device in accordance with claim 6, wherein the second temperature sensor is located between the outflow valve and the first temperature sensor.

9. The dispensing device in accordance with claim 1, wherein the first temperature sensor is configured as an electric sensor, an encapsulated thermocouple, an unencapsulated thermocouple, a resistor element, or as an NTC resistor.

10. The dispensing device in accordance with claim 1, wherein the first temperature sensor is configured as a contactless measuring infrared detector.

11. The dispensing device in accordance with claim 1, wherein the first temperature sensor and the second temperature sensor are configured in one piece as a spatially resolving contactless measuring infrared sensor.

12. The dispensing device in accordance with claim 1, wherein the feed device is at least partially configured as a porous solid, sintered body, nonwoven fabric or fiber stocking.

13. The dispensing device in accordance with claim 1, further comprising an anesthetic heater associated with the evaporator chamber, wherein:
   the anesthetic heater is configured to heat an anesthetic in the anesthetic reservoir as a gas stream heater or radiant heater; and
   the anesthetic heater is configured to be controlled by the control unit.

14. A dispensing device for anesthetic in a breathing gas stream, the dispensing device comprising:
   an evaporator chamber comprising a reservoir of anesthetic;
   a flow duct configured to receive an anesthetic-containing breathing gas stream from the evaporator chamber, the flow duct being downstream of the evaporator chamber with respect to a flow of the anesthetic-containing breathing gas stream;

a control unit;

a first temperature sensor;

an anesthetic feed device comprising an anesthetic evaporation surface, at least a portion of the anesthetic evaporation surface being arranged in the flow duct for evaporation of anesthetic in the flow duct, wherein the first temperature sensor is configured to detect the temperature of the portion of the anesthetic evaporation surface in the flow duct and is configured to send a first temperature signal to the control unit, the first temperature signal comprising the temperature of the portion of the anesthetic evaporation surface in the flow duct; and a second temperature sensor for detecting a temperature of the breathing gas stream in the flow duct and configured to send a second temperature signal to the control unit, the second temperature signal comprising the temperature of the breathing gas stream in the flow duct, wherein the control unit is configured to control an anesthetic concentration based on the first temperature signal and the second temperature signal.

15. A process for controlling and/or regulating an anesthetic concentration in a breathing gas stream, the process comprising:

providing a dispensing device for anesthetic, the dispensing device comprising a flow duct for an anesthetic-containing breathing gas stream, a control unit, a first temperature sensor, an anesthetic feed device arranged in the flow duct, the anesthetic feed device comprising an anesthetic evaporation surface for evaporation of anesthetic in the flow duct, wherein the first temperature sensor is configured to detect the temperature of the anesthetic evaporation surface and is configured to send a first temperature signal to the control unit and a second temperature sensor, wherein the second temperature sensor is configured to detect a temperature of the breathing gas stream in the flow duct and is configured to send a second temperature signal to the control unit and the control unit is configured to control an anesthetic concentration based on the first temperature signal and the second temperature signal, an evaporator chamber, in which an anesthetic reservoir is arranged upstream of the anesthetic evaporation surface, wherein the feed device is fluid-communicatingly connected to the anesthetic reservoir, and a connecting line connected to the evaporator chamber, the connecting line extending downstream of the evaporation chamber, the connecting line defining the flow duct, at least a portion of the anesthetic evaporation surface being located in the connecting line, the first temperature sensor being configured to detect the temperature of the portion of the anesthetic evaporation surface, the second temperature sensor being configured to detect the temperature of the breathing gas stream in the connecting line;

detecting a temperature of the anesthetic evaporation surface with the first temperature sensor; and detecting a temperature of the breathing gas stream in the flow duct by means of the second temperature sensor; and controlling and/or regulating an anesthetic concentration in the breathing gas stream based on the temperature of the anesthetic evaporation surface and the temperature of the breathing gas stream in the flow duct, with the control unit.

16. The process in accordance with claim 15, wherein:

the control unit comprises a desired value input for input of a desired value signal for the anesthetic concentration in the breathing gas stream, a determination module, which determines an anesthetic state point of anesthetic from the first temperature signal and the second temperature signal, and a regulating unit configured to regulate the anesthetic concentration in a patient feed line to the desired value signal;

the anesthetic concentration is determined by the determination module of the control unit based on the temperature of the anesthetic evaporation surface and the temperature of the breathing gas stream in the flow duct; and the breathing gas stream is regulated on the basis of the anesthetic concentration by the regulating unit of the control unit.

17. The process in accordance with claim 15, wherein:

the control unit comprises a calculation module, which is configured to determine a difference amount between the first temperature signal and the second temperature signal and a regulating unit configured to regulate the anesthetic concentration in a patient feed line to a desired value signal;

the calculation module of the control unit determines the difference amount and the anesthetic concentration is regulated based on the difference amount by the regulating unit.

18. The process in accordance with claim 15, wherein:

the control unit comprises a determination module, which determines an anesthetic state point of anesthetic from the first temperature signal and the second temperature signal; and the state point is associated with a defined anesthetic concentration in the breathing gas stream;

the anesthetic concentration is determined based on the state point in a state diagram for the anesthetic.

19. The process in accordance with claim 15, wherein the dispensing device further comprises an outflow valve, the second temperature sensor being located between the outflow valve and the first temperature sensor.

* * * * *